United States Patent [19]

Konomura

[11] Patent Number: 4,469,090
[45] Date of Patent: Sep. 4, 1984

[54] SUCTION CONTROL DEVICE FOR AN ENDOSCOPE

[75] Inventor: Yutaka Konomura, Tokyo, Japan

[73] Assignee: Olympus Optical Co., Ltd., Tokyo, Japan

[21] Appl. No.: 327,512

[22] Filed: Dec. 4, 1981

[30] Foreign Application Priority Data

Dec. 19, 1980 [JP] Japan .................................. 55-180228
Dec. 19, 1980 [JP] Japan .................................. 55-180229

[51] Int. Cl.³ .............................................. A61B 1/00
[52] U.S. Cl. ................................................... 128/4
[58] Field of Search ................................... 128/3–8, 128/276; 604/48

[56] References Cited

U.S. PATENT DOCUMENTS

| | | | |
|---|---|---|---|
| 3,517,669 | 6/1970 | Buono et al. | 128/276 |
| 3,707,972 | 1/1973 | Villari et al. | 128/349 R |
| 3,741,217 | 6/1973 | Ciarico | 128/349 |
| 3,791,379 | 2/1974 | Storz | 128/4 |
| 3,958,566 | 5/1976 | Funhata | 128/4 |
| 4,198,958 | 4/1980 | Utsugi | 128/5 |
| 4,211,214 | 7/1980 | Chikashige | 128/4 |
| 4,261,343 | 4/1981 | Ouchi et al. | 128/4 |

Primary Examiner—John D. Yasko
Assistant Examiner—J. L. Kruter

[57] ABSTRACT

A suction control device of an endoscope comprises an outer cylinder connected with a channel at one end and having an opening at the other end, an inner cylinder opening at either end and inserted in the outer cylinder so as to be able to move axially between a first position on one end side of the outer cylinder and a second position on the other end side of the outer cylinder, thereby forming an annular space defined between the inner cylinder and the outer cylinder, a first rugged ring formed on one end of the inner cylinder, a second rugged ring formed on the inner peripheral surface of the outer cylinder so as to come closely in contact with the first rugged ring to cut off the communication between the space and the channel when the inner cylinder is moved to the first position, and a coupling piece disposed on the other end of the outer cylinder so as to cut off the space from the atmosphere and supporting the inner cylinder so as to allow the space to communicate with the channel. A suction tube is connected with the space between the coupling piece and the first rugged ring, the outer cylinder having a communication hole for connecting the space with the atmosphere between the coupling piece and the first rugged ring.

8 Claims, 8 Drawing Figures

FIG. 7
FIG. 8
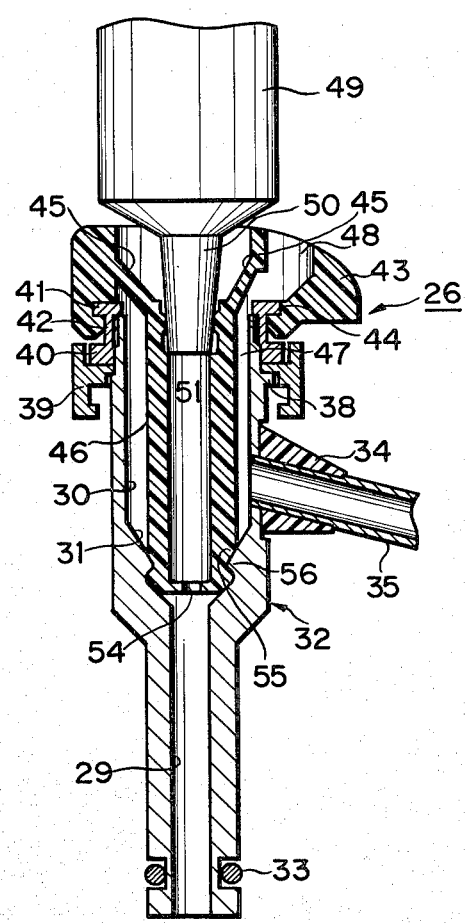
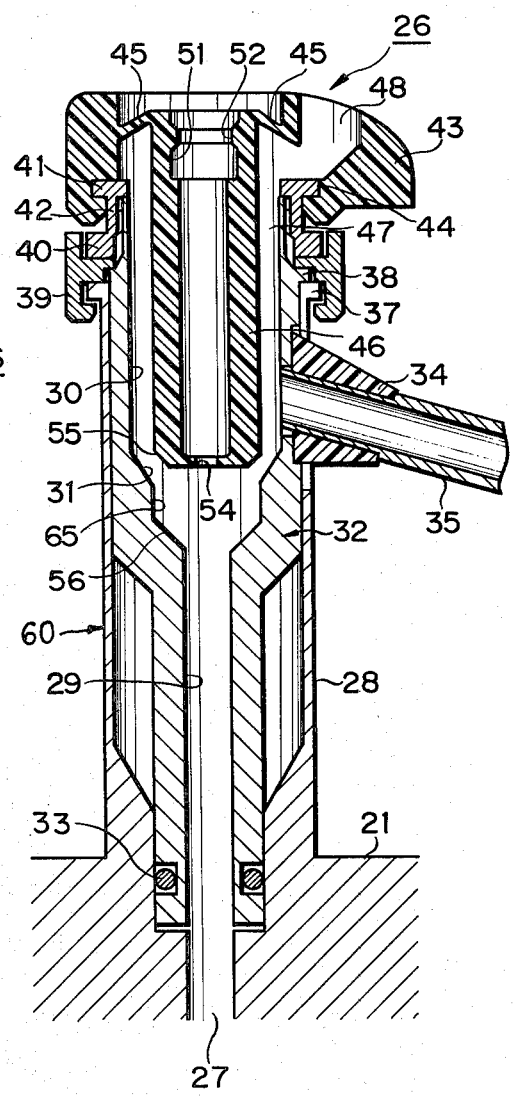

SUCTION CONTROL DEVICE FOR AN ENDOSCOPE

BACKGROUND OF THE INVENTION

This invention relates to a suction control device for an endoscope adapted to suction, air and water feeding, insertion of forceps or other treatment appliances, etc., by means of a channel.

In general, a suction control device of an endoscope is used for removing mucus, waste, etc., from the body cavity by suction. Such a suction control device, however, is so designed as to be able to be also used for insertion of a treatment appliance and injection of a medical fluid into the body cavity.

Conventionally, the suction control device of this type is constructed as shown in FIG. 1. In FIG. 1, numeral 1 designates an outer cylinder which has its peripheral wall connected with a suction tube 2 and its lower end with a channel of the endoscope. Disposed in the outer cylinder 1 is a guide cylinder 5 which consists of a first cylinder portion 3 and a second cylinder portion 4 with its lower end screwed in the upper end of the first cylinder portion 3, defining a space portion 6 between these two cylinders. A slide cylinder 7 is fitted in the guide cylinder 5, and is elastically held by means of a compression spring 8 interposed between the outer peripheral surface of the slide cylinder 7 and the inner peripheral surface of the guide cylinder 5. A support cylinder 10 is coupled with the lower end of the slide cylinder 7 by means of a coupling cylinder 9. Held in the support cylinder 10 is a slider 12 having a central communication hole 11 through which a treatment appliance is passed. Further, a communication hole 13 connecting the space portion 6 with the interior of the guide cylinder 5 is bored through the peripheral wall of the first cylinder portion 3 below the slider 12. A cap 14 is fitted on the top of the outer cylinder 1. The cap 14 is provided with a holding hole 15 fitted airtightly with the upper end portion of the guide cylinder 5 and an air hole 16 for connecting the space portion 6 with the open air.

In sucking mucus or waste from a body cavity, both the holding hole 15 and the air hole 16 are blocked up with a finger. Then, a sucking force in the suction tube 2, having so far been sucking the open air through the air hole 16 and the space portion 6, acts on the interior of the body cavity through the channel, as indicated by arrow a in FIG. 1. As a result, the mucus or waste in the body cavity is sucked into the suction tube 2. In making both treatment with use of the treatment appliance and suction at the same time, the appliance is inserted into the channel through the slide cylinder 7 and the communication hole 11 of the slider 12, and the air hole 16 is blocked up with a finger. In liquid feeding, moreover, the distal end portion of an injector is fitted in the slide tube 7, and the slide tube 7 is pushed and slidden against the restoring force of the spring 8 to cause the communication hole 13 to be blocked up by the slider 12 which shifts its position together with the slide cylinder 7. Then, the interior of the guide cylinder 5 is cut off from the space portion 6 to allow a liquid to be fed from the injector into the body cavity through the channel.

In the prior art suction control device of the above-mentioned construction, however, the three cylinders, i.e., the outer cylinder 1, the guide cylinder 5, and the slide cylinder 7, are required for the versatility of the device, and moreover the spring 8 need be interposed between the guide cylinder 5 and the slide cylinder 7. Thus, the number of components required is increased, and the assembly work is complicated to result in an increase in cost as well as a reduction in productivity. Since the slider 12 to block up the communication hole 13 at liquid feeding is slidably fitted in the guide cylinder 5, it is impossible securely to seal the sliding surface of the slider 12. Accordingly, part of the liquid delivered from the injector may be sucked through the space portion 6 into the suction tube 2, prohibiting satisfactory feeding of the liquid into the body cavity. Moreover, the aforesaid complicated construction makes it impossible to wash out mucus or waste part of which would inevitably penetrate to the region of the spring 8 and its vicinities through the gap between the respective sliding surfaces of the guide cylinder 5 and the support cylinder 10 at the suction of such mucus or waste from the body cavity.

SUMMARY OF THE INVENTION

The object of this invention is to provide a suction control device for an endoscope using fewer cylinders for simplified construction, and capable of secure disconnection of the channel side from the suction tube side at liquid feeding without the use of any sliding surface.

BRIEF DESCRIPTION OF THE DRAWINGS

FIGS. 2 to 7 show a suction control device of an endoscope according to an embodiment of this invention, in which FIG. 2 is a general perspective view of the endoscope, FIG. 3 is a sectional view of the suction control device, FIG. 4 is a plan view of a cap, FIG. 5 is a partially broken side view of the device illustrating a sucking operation, FIG. 6 is a sectional view of the device illustrating a forceps operation, and FIG. 7 is a sectional view of the device illustrating a liquid feeding operation; and FIG. 8 is a sectional view similar to FIG. 3 showing a modification of engaging portions.

DETAILED DESCRIPTION OF THE PREFERRED EMBODIMENT

Figure 1:
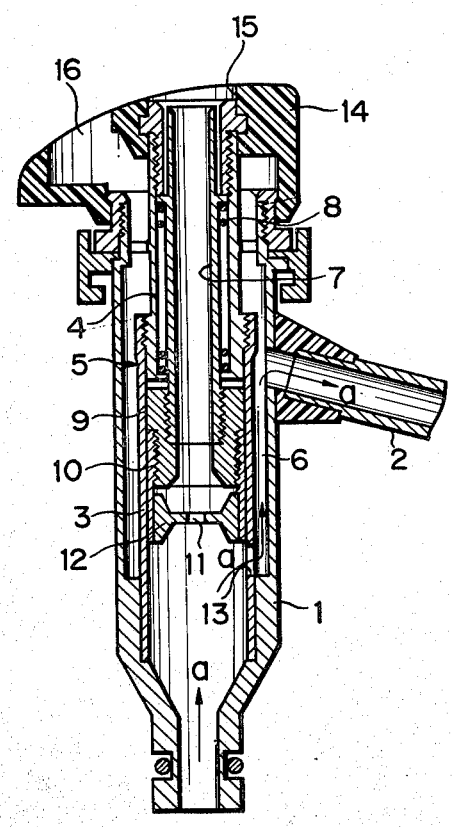
FIG. 1 is a sectional view of a prior art suction control device for an endoscope.
Figure 2:
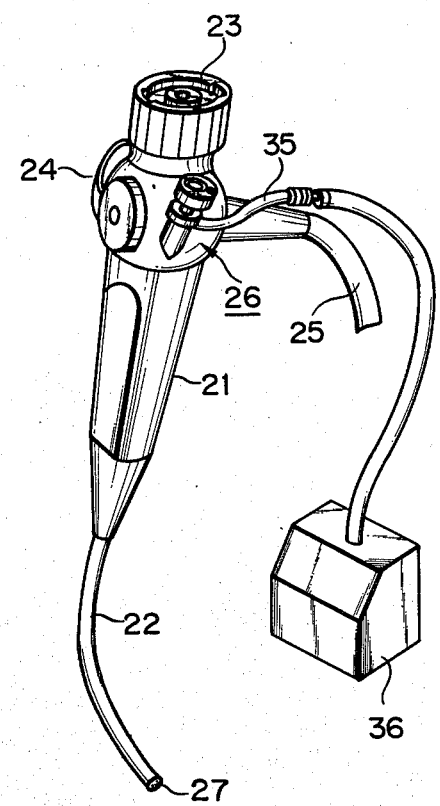

Now there will be described a suction control device of an endoscope according to an embodiment of this invention with reference to the accompanying drawings. As shown in FIG. 2, the endoscope comprises a control section 21 and an insertion section 22 connected with the control section 21 at the proximal end. The control section 21 is provided with an eyepiece portion 23, a control knob 24 for bending the distal end portion of the insertion section 22, a light guide cable 25 connected with a light supply unit (not shown), and a suction control device 26. In the insertion section 22, a channel 27 extends from the control section 21 to the distal end of the insertion section 22.

Figure 3:
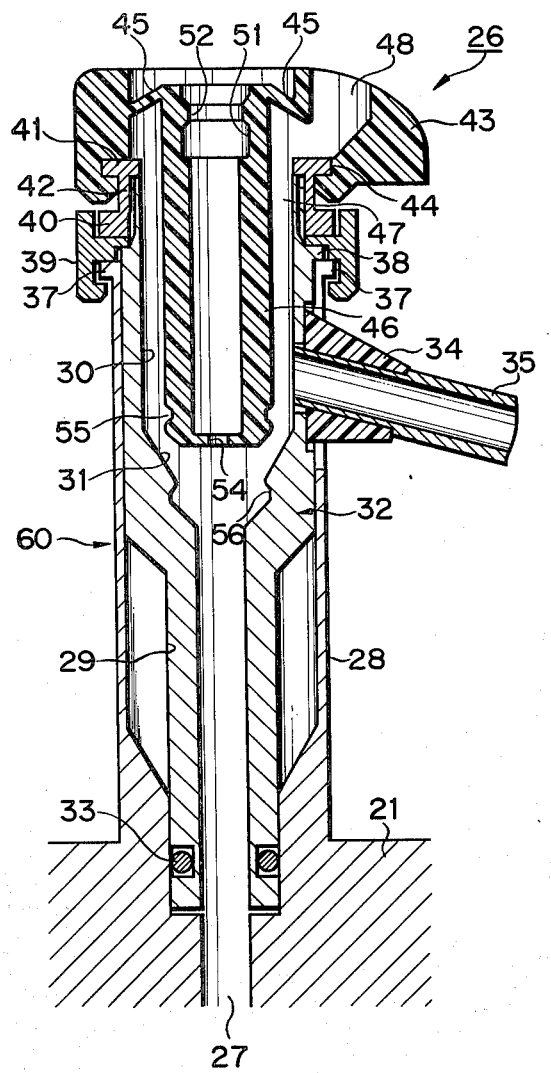
Figure 4:
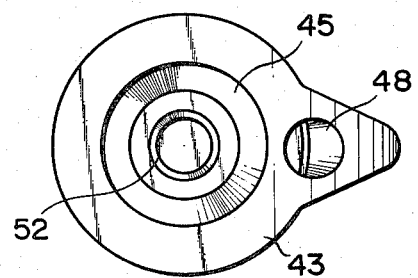

The aforesaid suction control device 26 is constructed as shown in FIGS. 3 and 4. From the control section 21 of the endoscope protrudes an integrally formed support cylinder 28 which communicates by means of the control section 21 with the channel 27 opening at the distal end of the insertion section 22 and has an open end. Fitted in the support cylinder 28 is a first cylinder body 32 having a small-diameter portion 29 and a large-diameter portion 30 coupled by means of a taper portion 31 and opening at the lower or inner end. The lower end portion of the small-diameter portion 29 of the first cylinder body 32 is inserted in the channel 27 and coupled airtightly therewith by means of an O-ring 33. One end of a suction tube 35 is connected with the peripheral wall of the large-diameter portion 30 of the first cylinder body 32 by means of a connector 34. The other end of the suction tube 35 communicates with a suction unit 36 shown in FIG. 2.

Stoppers 37 and 38 protrude from the outer periphery of the upper end of the support cylinder 28 and from the outer peripheral wall of the first cylinder body 32 near the top portion thereof, respectively. The first cylinder body 32 is removably fixed to the support cylinder 28 by means of a bayonet ring 39 which engages the stoppers 37 and 38. Further, a pressing cylinder 42 with a pressing flange 40 and a fitting flange 41 at both ends is screwed on the outer periphery of the upper end portion of the first cylinder body 32. Pressed by the pressing flange 40 of the pressing cylinder 42, the bayonet ring 39 is kept from loosening. The pressing cylinder 42 is crowned with a cap 43 formed of an elastic material, such as rubber and synthetic resin, with an annular fitting groove 44 in the inner peripheral surface of the cap 43 fitted on the fitting flange 41.

Thus, the first cylinder body 32, the bayonet ring 39, the pressing cylinder 42, and the cap 43 form an outer cylinder 60 which communicates with the channel 27 at one end and has an opening at the other end. The cap and first cylinder body of the outer cylinder 60 may be formed integrally. In other words, the outer cylinder 60 need not always have the removable cap.

Figure 6:
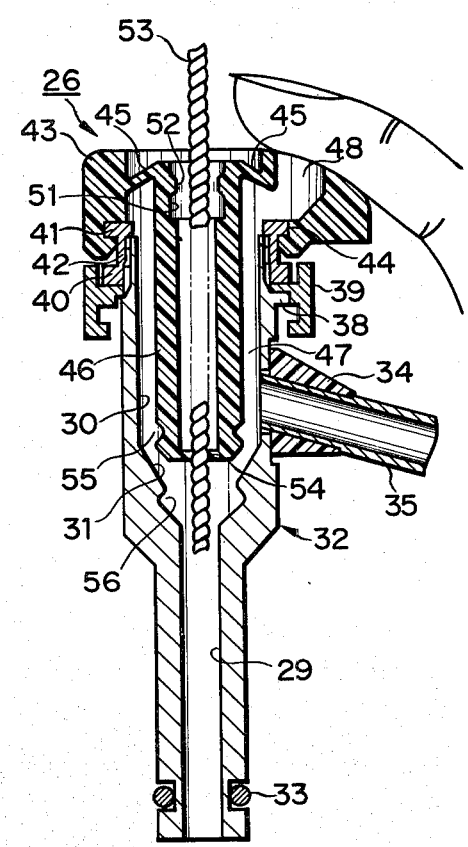

The inner peripheral surface of the cap 43 is connected with the outer peripheral edge of an annular coupling piece 45 capable of expansion and contraction, as well as of elastic deformation. The inner peripheral edge of the coupling piece 45 is connected with the upper end of a second cylinder body 46 which forms an inner cylinder. Preferably, the coupling piece 45 and the second cylinder body 46 are formed integrally with the cap 43 out of an elastic material. The second cylinder body 46 is inserted coaxially in the outer cylinder 60 so as to have its lower end located inside the outer cylinder 60 and to be able to move axially between a first position on the lower end side of the outer cylinder 60 and a second position, as shown in FIG. 3, on the upper end side of the outer cylinder 60. The second cylinder body 46 is supported on the outer cylinder 60 by means of the coupling piece 45, and is normally urged toward the second position of FIG. 3 by the elastic force of the coupling piece 45. The second cylinder body 46 has at the upper end an opening and at the lower end a narrow communication hole 54 through which a forceps 53 as a treatment appliance, as shown in FIG. 6, is passed tight. An annular space portion 47 is defined between the outer peripheral surface of the second cylinder body 46 and the inner peripheral surface of the large-diameter portion 30 of the first cylinder body 32. The space portion 47 is blocked up at the top by the coupling piece 45 to be cut off from the atmosphere. Formed in the cap 43 is a communication hole 48 extending from the top of the cap 43 to that part of the space portion 47 between the coupling piece 45 and the opening of the suction tube 35 and connecting the space portion 47 with the atmosphere.

The second cylinder body 46 is provided, on the inner peripheral surface of its upper end portion, with a step portion 51 in which a distal taper portion 50 of an injector 49 as shown in FIG. 7 is fitted. From the inner peripheral surface of the step portion 51 protrudes an annular projection 52 which is to press on the taper portion 50 to hold the same. A first rugged ring 55 as an engaging member formed on the outer peripheral surface of the lower end portion of the second cylinder body 46 is to be fitted elastically and airtightly in a second rugged ring 56 as another engaging member formed on the taper surface of the taper portion 31 of the first cylinder body 32 when the second cylinder body 46 is disposed by elastic deformation of the coupling piece 45, as shown in FIG. 7. The first and second rugged rings 55 and 56 are so designed as to be able to be disengaged from each other with a smaller force than a pulling force needed to remove the pressure contact between the taper 50 of the injector 49 and the projection 52. Therefore, the second rugged ring 56 can be disengaged from the first rugged ring 55 to restore the second cylinder body 46 to the second position before the taper portion 50 of the injector 49 is removed from the step portion 51.

Figure 5:
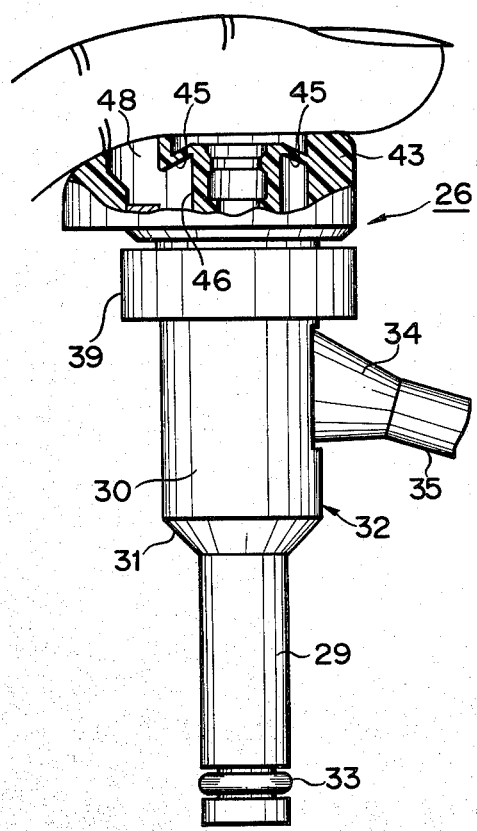

Now there will be described the operation of the above-mentioned construction. First, when the suction unit 36 is actuated in the state shown in FIG. 3, a sucking force is produced in the suction tube 35. Since the atmosphere is sucked into the suction tube 35 through the communication hole 48 and the space portion 47, however, the sucking force is prevented from acting on the interior of a body cavity through the channel 27. In sucking mucus or waste from the body cavity, the whole upper portion of the cap 43, i.e., the communication hole 48, and the top opening of the second cylinder body 46 are blocked up with an operator's finger, as shown in FIG. 5. Then, the communication between the space portion 47 and the atmosphere is cut off, so that the sucking force from the suction tube 35 acts on the channel 27 to cause the mucus or waste in the body cavity to be sucked into the suction tube 35 through the channel 27 and the space portion 47.

When using the forceps 53, moreover, the forceps 53 is inserted into the top opening portion of the second cylinder body 46, passed through the communication hole 54 of the second cylinder body 46, and then led into the channel 27, as shown in FIG. 6. In this state, the forceps 53 is fitted airtightly in the communication hole 54, so that the space portion 47 is prohibited from communicating with the atmosphere by means of the second cylinder body 46. When it is necessary to perform sucking operation while using the forceps 53, the communication between the space portion 47 and the atmosphere may be cut off to allow the suction of mucus or waste from the body cavity by blocking up only the communication hole 48 of the cap 43 with a finger.

In injecting a liquid such as a medical fluid, furthermore, the distal taper portion 50 of the injector 49 is fitted in the step portion 51 of the second cylinder body 46, as shown in FIG. 7. When the injector 49 is then pushed in to elastically deform and extend the coupling piece 45, thereby driving the second cylinder body 46 deep into the first cylinder body 32, the first rugged ring 55 on the outer peripheral surface of the lower end portion of the second cylinder body 46 is fitted in the second rugged ring 56 on the taper surface of the taper portion 31 of the first cylinder body 32 to cut off thoroughly the communication between the channel 27 and the space portion 47. Accordingly, if the liquid is caused to run out of the injector 49 in this state, then it will securely be introduced into the body cavity through the channel 27 without being affected by the sucking force from the suction tube 35.

Thus, according to the suction control device 26 of the aforementioned construction, the communication between the channel 27 and the space portion 47 communicating with the suction tube 35 can securely be cut off by displacing the second cylinder body 46, which is movably held in the first cylinder body 32, to couple the first and second rugged rings 55 and 56 by press fit. As a result, the structure of the device may be simplified to facilitate and secure overall cleaning, and to prohibit the sucking force from the suction tube 35 from leaking to the channel side at liquid feeding to cause the liquid to be sucked into the suction tube 35.

Referring now to FIG. 8 corresponding to FIG. 3, there will be described a modification of the first and second engaging portions. In the description of this modification to follow, like reference numerals used in FIG. 3 refer to like portions.

A step portion 65 is formed on a taper portion 31 of a first cylinder body 32. The bottom of the step portion 65 has a taper surface 56 which, declined toward the central axis of the cylinder body 32, forms the second engaging portion. Formed on the outer peripheral side of the lower end of the second cylinder body 46, on the other hand, is a taper surface 55 which, having substantially the same inclination as that of the taper surface 56, forms the first engaging portion.

Although the first cylinder body 32 is inserted in the support cylinder 28 in the above embodiment, the support cylinder 28 may be used as the first cylinder body. Further, in the aforesaid embodiment, the second cylinder body 46 is formed integrally with the cap 43, connected therewith by means of the coupling piece 45. It is to be understood, however, that a device with the same function of the above-mentioned embodiment may be obtained without integrally forming those members.

In the above-mentioned embodiment, moreover, the coupling member is formed of a member capable of expansion and contraction, as well as of elastic deformation. Alternatively, however, the coupling member may be formed of a member having only one of those properties. Such member may, for example, be a bellows connected with the outer and inner cylinders at the outer and inner peripheral edges, respectively.

According to this invention, as described above, there may be provided a suction control device with a double-cylinder construction including outer and inner cylinders simplified as compared with the conventional triple-cylinder construction despite the same function. Accordingly, the number of components used in the device can be reduced, and overall cleaning of the device can securely be performed with ease. In liquid feeding, moreover, the press-fit engagement between the engaging portions on the outer and inner cylinders disconnects the channel side securely from the suction tube side, so that the liquid will never be sucked into the suction tube.

What is claimed is:

1. In an endoscope having a suction control device for selectively connecting a passageway and a suction tube of said endoscope, comprising:
a control device having a channel;
an outer cylinder connected with said channel at one end thereof and having an opening at the other end thereof to and communicating with the atmosphere;
an inner cylinder having two faced; said cylinder open at either end face thereof and inserted in and coupled to said outer cylinder so as to have one end thereof located inside said outer cylinder and being movable longitudinally between a first position and a second position, a space being defined between an outer peripheral surface of said inner cylinder and an inner peripheral surface of said outer cylinder;
a first engaging portion including a first tapered portion formed on one end face of said inner cylinder;
a second engaging portion means including a second tapered portion formed on said inner peripheral surface of said outer cylinder so as to come into angular abutting contact with the first tapered portion of said inner cylinder to cut off the communication between said space and said channel when said inner cylinder is moved to said first position;
a coupling member disposed on said other end of said outer cylinder so as to cut off said space from the atmosphere and supporting said inner cylinder so as to allow said space to communicate with said channel in said second position; and
means for connecting said suction tube with said space between said coupling member and said first engaging portion,
said outer cylinder having a communication hole for connecting said space with the atmosphere between said coupling member and said first engaging portion.

2. A suction control device according to claim 1, wherein said outer cylinder includes a first cylinder body communicating with said channel at one end and opening at the other end and a cap blocking up the opening of said outer cylinder body, and said inner cylinder includes a inner cylinder body supported on said cap by means of said coupling member.

3. A suction control device according to claim 2, wherein said first engaging portion is an elastic body formed on one end of said inner cylinder body.

4. A suction control device according to claim 3, wherein said first engaging portion includes a convex ring, and said second engaging portion includes a concave ring engagedly receiving said convex ring to cut off the communication between said space and said channel.

5. A suction control device according to claim 4, wherein said first engaging portion includes a concave ring adjacent to said concave ring, and said second engaging portion includes a convex ring adjacent to said concave ring thereof and engagedly receiving the concave ring of said first engaging portion.

6. A suction control device as in claims 1, 2, 3, 4, or 5, wherein said coupling member includes an elastic piece connected between said cap and the other end of said inner cylinder and urging said inner cylinder toward said second position.

7. A suction control device according to claim 6, wherein said elastic piece is capable of expansion and contraction.

8. A suction control device according to claim 6, wherein said cap and said inner cylinder are elastic bodies formed integrally with said elastic piece.

* * * * *